(12) United States Patent
Söremark

(10) Patent No.: US 6,358,478 B1
(45) Date of Patent: Mar. 19, 2002

(54) METHOD AND APPARATUS FOR TREATMENT OF FLUIDS

(75) Inventor: Rune Söremark, Bromma (SE)

(73) Assignee: Benrad Aktiebolag, Bromma (SE)

( * ) Notice: Subject to any disclaimer, the term of this patent is extended or adjusted under 35 U.S.C. 154(b) by 0 days.

(21) Appl. No.: 09/358,648

(22) Filed: Jul. 23, 1999

Related U.S. Application Data

(63) Continuation of application No. 08/860,444, filed as application No. PCT/SE95/01575 on Dec. 22, 1995, now Pat. No. 5,961,920.

(30) Foreign Application Priority Data

Dec. 28, 1994 (SE) ............................................. 9404555
Dec. 28, 1994 (SE) ............................................. 9404555

(51) Int. Cl.[7] ............................................. A61L 2/10
(52) U.S. Cl. ........................ 422/121; 422/122; 250/435
(58) Field of Search ............................... 422/4, 23, 24, 422/29, 30, 122, 121, 123, 292; 250/432 R, 435; 210/760

(56) References Cited

U.S. PATENT DOCUMENTS

| | | | |
|---|---|---|---|
| 4,990,260 A | 2/1991 | Pisani | 210/664 |
| 4,990,311 A | 2/1991 | Hirai et al. | 422/4 |
| 5,186,907 A | 2/1993 | Yanagi et al. | 422/186.3 |
| 5,288,461 A | 2/1994 | Gray | 422/24 |
| 5,961,920 A | * 10/1999 | Soremark | 422/24 |

FOREIGN PATENT DOCUMENTS

EP   0 570 898 A1   11/1993   ............. A61L/2/14

OTHER PUBLICATIONS

Kiyotaka, Tanaka. Abstract of JP 02243121A. Sep. 1990, see Abstract.*

* cited by examiner

Primary Examiner—Elizabeth McKane
(74) Attorney, Agent, or Firm—Kilpatrick Stockton LLP

(57) ABSTRACT

The invention relates to a method for treatment of fluids, the invention being characterized in that ozone is generated in the medium, which ozone is exposed to UV radiation at the same time as it is being generated, so that the ozone is broken down and free radicals are obtained. The invention also relates to an apparatus in accordance with the method, which apparatus comprises an enclosure (1) provided with at least one inlet (2) and at least one outlet (3). The apparatus is characterized in that an oxidizing member (4) is arranged in the enclosure (1) and generates ozone and at the same time breaks down the ozone to free radicals.

15 Claims, 3 Drawing Sheets

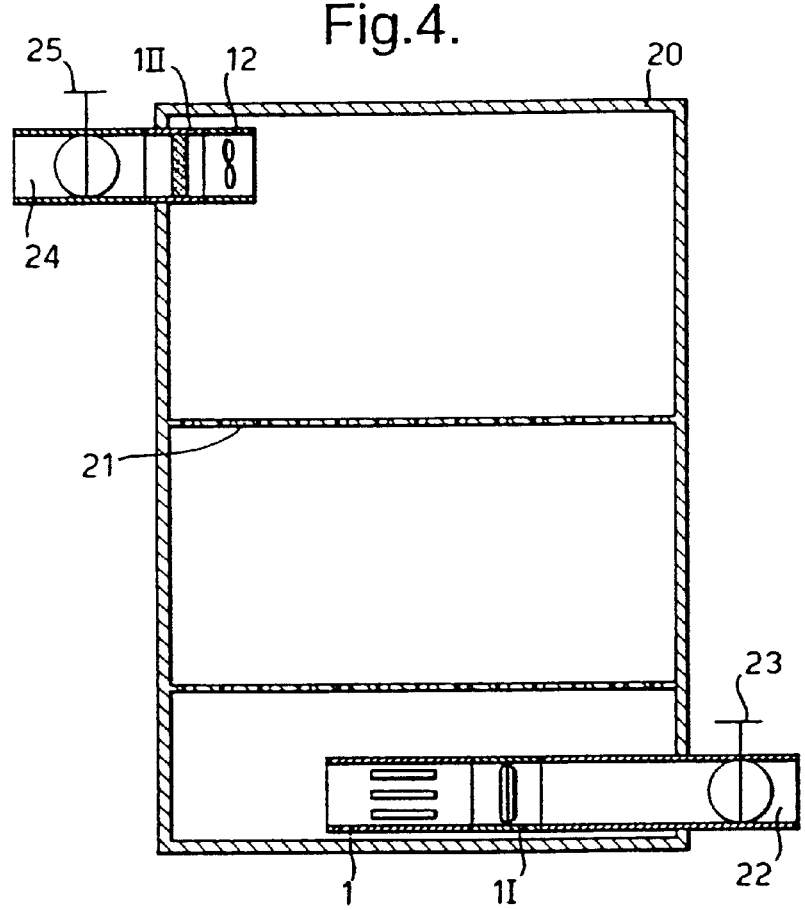
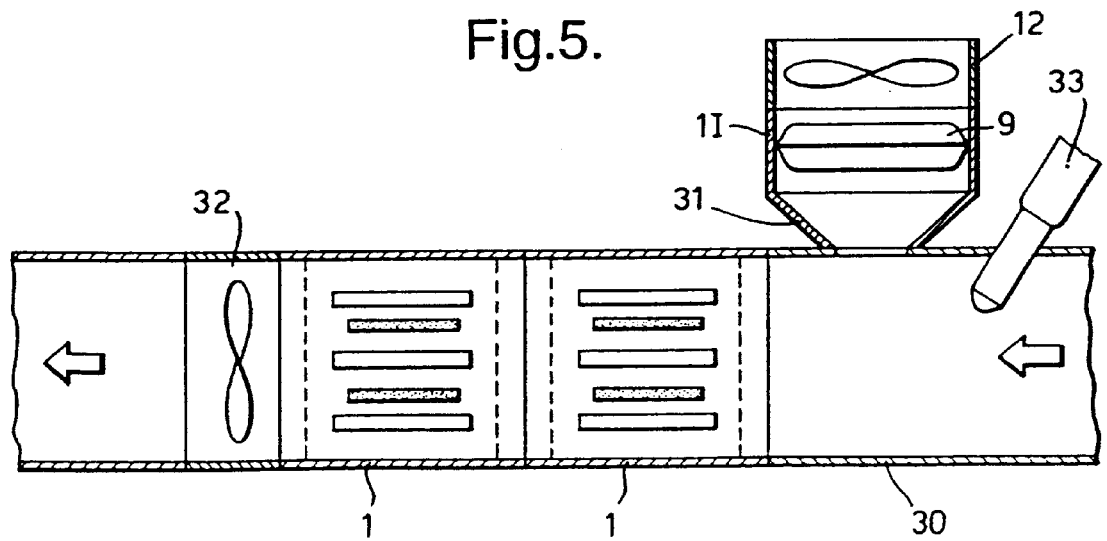

METHOD AND APPARATUS FOR TREATMENT OF FLUIDS

CROSS REFERENCE TO RELATED APPLICATIONS

This is a continuation of application Ser. No. 08/860,444, filed Sep. 19, 1997 now U.S. Pat. No. 5,961,920 which is a 371 PCT/SE95/01575.

TECHNICAL FIELD

The present invention relates to a method and an apparatus for treatment of fluids. Fluids will in this context be understood as gases and liquid media as well as suspensions and emulsions.

STATE OF THE ART

In recent years, ever greater demands have been placed on the environment wherever man has been present. There are many reasons for this. One is that modem man's mobility between different geographical areas means that pathogens find fertile breeding ground for development of extremely virulent strains. These can give rise to serious diseases for which there are as yet no cures.

In hospitals, pathogens can be transmitted from one patient to other persons—both patients and nursing staff—and these pathogens are transmitted further by direct contact or indirectly via instruments, clothes, food or the like. Hospital textiles are contaminated to a greater or lesser extent with pathogens. One problem is that the washing methods are not completely satisfactory as regards removal of pathogens from hospital textiles. In addition, there is a need for better and simpler methods for sterilization, on the one hand of sensitive equipment such as, for example, endoscopy instruments and catheters which do not tolerate conventional sterilization methods, and, on the other hand, in operations where instruments need to be sterilized directly and quickly as they may have become contaminated during surgery (the surgeon may, for example, drop special instruments, implants and the like).

Other environments where pathogens and other types of pollution are spread and which often have problems with poor air are schools, day nurseries, food shops, kitchens, ship cabins, industrial premises and the like, especially in poorly ventilated premises. A further problem area is "sick houses" with, for example, radon, mould, hexamine and the like, as well as premises which are being painted, papered, floored, etc.

Water is another area where ever greater demands are being placed both on purity and on minimizing the environmental pollution when treating drinking water and waste water.

These media, and media contaminated in other ways, have created considerable unrest and the need for effective decontamination processes.

A number of proposals for dealing with the abovementioned problems have been put forward during the years, such as better ventilation, various types of filters and chemicals for purification of air and water. Since chlorine itself is a burden on the environment, methods have been developed in several countries for purifying water with ozone ($O_3$) in drinking water installations and bathing facilities, and also ozone dissolved in water for cleaning, disinfection and sterilization of articles. The reaction capacity of ozone (2.07 V electrochemical oxidation potential) is ascribed to the fact that it is a powerful oxidant. The high chemical reactivity is coupled with the unstable electron configuration which seeks electrons from other molecules, which thus means that free radicals are formed. In this process, the ozone molecule is broken down. By means of its oxidizing effect, the ozone acts rapidly on certain inorganic and organic substances. Its oxidizing effect on certain hydrocarbons, saccharides, pesticides, etc., can mean that ozone is a good choice of chemical in certain processes. A combination of ozone, oxygen, hydroperoxide and UV radiation means that the reaction proceeds much more quickly and more efficiently by virtue of the generation of more free radicals.

The inactivation of microorganisms with the aid of ozone and radicals is considered as an oxidation reaction. The membrane of the microorganism is the first to be attacked. Within the membrane/cell wall, the ozone and the radicals destroy nuclear material inside the cell/virus/spore. The inactivation reaction in the case of most microorganisms occurs within minutes, depending on the ozone dose and the amount of free radicals which are formed.

In most cases, ozone is used in the form of ozone water for removing or reducing chemicals, dyes, heavy metals, odour, and destroying pathogens in water-purification works, removing algae, fungus, deposits, and for reducing the use of chemicals in water-cooling systems and heat exchangers, treating water in pools, aquariums and fish farms, sterilizing bottles and jars which are used in the beverage and food industry.

Despite its solubility in cold water, ozone is broken down (=consumed) quickly, as is the case in air, which gives a great many different radicals and more or less stable by-products such as aldehydes, bromate and carboxylic acids. The degree of breaking down depends on the pH, the substance which is exposed and the temperature. Certain substances are broken down easily by the ozone. However, the majority of substances and molecules are oxidized more efficiently by free radicals which are formed by ozone and the media treated by ozone. Certain free radicals have a higher electrochemical oxidation potential than ozone (2.8 V for hydroxyl radical and 2.42 for oxygen (singlet)). Examples of common oxidants which can be formed are hydroxyl radicals ($HO^-$), peroxyl radicals ($RO_2^-$), (singlet) oxygen ($^1O_2$), diradicals ($R^-$—$O^-$) and alkoxy radicals ($RO^-$).

Oxidation of organic molecules is best understood on the basis of the two similar paths for reactions of $HO^-$, $RO^-$, $RO_2^-$ and $^1O_2$ radicals. Most organic chemicals which are mixed with air as gases are oxidized by $HO^-$ radicals. Aliphatic molecules give $RO_2^-$ radicals which can undergo various reactions, the most significant of which is the conversion to an alkoxyl radical ($RO^-$) via NO. Reactions of $RO^-$ radicals are rapid and produce new carbon radicals by cleaving or by intramolecular transfer of H atoms. A reaction cycle of intramolecular transfer of H atoms, formation of a new $RO_2^-$ radical, conversion to the corresponding $RO^-$ radical and, finally, a further intramolecular reaction can lead to highly oxidized carbon chains.

Aromatic molecules oxidize quickly with $HO^-$ radicals, which forms carbon radicals and phenols. Singlet oxygen ($^1O_2$) is important for oxidizing a great many organic chemicals, including amino acids, mercaptans, sulphides and polycyclic aromatic hydrocarbons. These too are rapid oxidation processes.

Consequently, ozone reacts with contaminants via two essential pathways. It can react directly, as molecular ozone ($O_3$), by reactions which are selective. In general, activated compounds (phenol, resorcinol, salicylate), olefins and simple amines are expected to react with molecular ozone, as are certain microorganisms.

Alternatively, ozone can react with contaminants via an indirect route, in which the free radicals, which are produced by decomposition of ozone and by reactions, serve as oxidants. These indirect reactions of the radical type are rapid and non-selective.

Organic contaminants which react slowly with molecular ozone, such as aliphatic acids, aldehydes, ketones and aromatic hydrocarbons, react to a greater extent via the non-selective radical route. Thus, the conditions which break down ozone, such as UV radiation, favour indirect and non-selective reactions where the free radicals formed are strong oxidants. In the case of air, the radical route has a predominant role in most oxidation processes. Even in situations where the first oxidation reaction between the ozone and contaminants takes place via the direct route, radicals are generated so that the subsequent oxidation takes place effectively and rapidly by means of radical reaction processes.

Since the radicals are non-selective, they can oxidize all reduced substances and are not limited to specific classes of contaminants, as is the case with molecular ozone.

As has been mentioned, UV radiation favours a rapid decomposition of ozone with subsequent formation of radicals. In those cases where contaminants absorb UV radiation (for example, tetrachloroethylene), direct photolysis of the pollutant contributes to the degree of oxidation.

In many apparatuses, ozone is generated by corona discharges. When a 6–7 eV electron interacts with an oxygen molecule ($O_2$), dissociation takes place. The oxygen atoms (O+O) which are formed are immediately combined with oxygen molecules to form ozone ($O_3$).

It is also known that UV radiation with a wavelength of approximately 183 nm gives rise to ozone in air. However, it is difficult to make such lamps adequately effective for production of ozone in the large quantities which may be needed in many cases.

A number of trials on purifying air with ozone have been carried out, such as described, for example, in the patent U.S. Pat. No. 5,186,907. The patent describes an apparatus for treatment of organic waste gases which contain toxic components as organic solvents. The gases are sucked into an enclosure by a fan and are initially exposed in the said enclosure to a first oxidizing member, for example a UV lamp, which causes oxygen in the air to form ozone. The oxidizing effect of the ozone means that most of the organic solution forms peroxide. The peroxide is then irradiated by a second oxidizing member, in this case a UV lamp which emits radiation at a wavelength of 365 nm, so that the peroxide is broken down almost completely to carbon dioxide, water and inorganic gas components by oxidation. At the same time, those parts of the organic gas which were not oxidized by the first oxidizing member and the ozone will be oxidized and broken down by the second oxidizing member.

The apparatus in accordance with the above is targeted at organic solvents such as isopropyl alcohol, where the first oxidizing member converts the solution to peroxide, which is then oxidized by the radiation from a UV lamp at a wavelength of 365 nm. This apparatus has a narrow scope of application, specifically for treatment of certain defined organic solvents.

In the patent U.S. Pat. No. 5,260,036, a method of photochemically oxidizing gaseous halogenic organic compounds is disclosed. According to the patent, the compounds are exposed to UV light to oxidize them into gaseous oxidation products and reacting the gaseous oxidation products with a surface inside an oxidation chamber, where the surface a material which is chemically reactive with the gaseous oxidation products in order to produce solid reaction products incorporated in side walls of the chamber. This chemically sorbant internal surface material has a life of 1–3 months.

It is evident from what has been described above that ozone can be used to good effect for purifying, disinfecting and sterilizing within certain areas and in the case of certain substances. The use of ozone for the purpose of obtaining free radicals therefrom should, however, considerably increase the efficiency, the scope of application and the substances which can be rendered safe. This procedure has not until now been used effectively.

SUMMARY OF THE INVENTION

The object of the invention is to tackle the abovementioned set of problems with purification and disinfection of contaminated media such as air, water and solid articles, and also disinfection and sterilization of articles in a more efficient manner than has been possible with previous methods and apparatuses. This is achieved by means of a procedure and apparatus according to the characterizing clauses of Patent Claim 1 and Patent Claim 5.

DESCRIPTION OF THE FIGURES IN THE DRAWINGS

The procedure using preferred embodiments of apparatuses according to the invention will be described in detail hereinbelow and with reference to the attached drawings, in which:

FIG. 4 shows a variant of the apparatus and an example of the use for production of a sterilizing gaseous fluid for sterilization of solid articles in a closed space; and FIG. 5 shows another variant of the apparatus according to the invention adapted for a liquid-state fluid.

DETAILED DESCRIPTION OF THE INVENTION

The procedure according to the present invention is as follows. The medium which is to be treated is preferably introduced into some form of enclosure. In the enclosure, the medium is exposed to UV radiation with a spectral distribution within the range of 180–400 nm. The wavelength of 183.7 nm in particular converts the oxygen in the medium to ozone molecules ($O_3$). The ozone molecules formed are at the same time decomposed by radiation within the abovementioned wavelength range, especially at a wavelength of 254 nm. At the same time, the $O_2$ formed is broken down to form atomic oxygen. In order to increase the efficiency during generation of free radicals, in particular HO⁻ radicals, oxides are added as catalysts. In order to obtain a greater amount of ozone and consequently more free radicals, further ozone is generated before the medium is irradiated.

Figure 1:
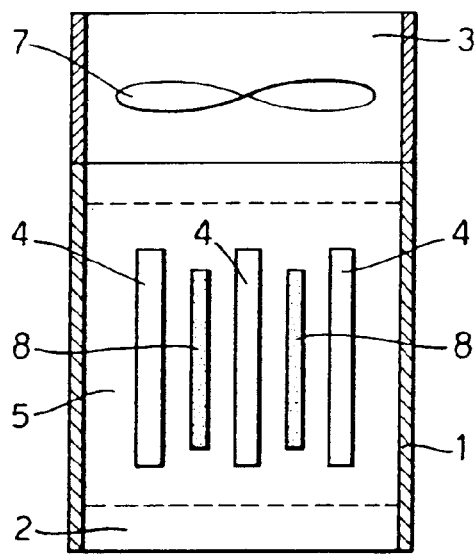
FIG. 1 shows a cross-section of an apparatus according to the present invention.

An apparatus which is based on the abovementioned method is shown in FIG. 1. The apparatus is designed as an enclosure 1 with at least one inlet 2 and one outlet 3. An oxidizing member 4 is arranged in the enclosure 1, in the preferred embodiment a number of UV lamps with a spectral distribution within the range of 180–400 nm. The lamps 4 are preferably placed in such a way that the entire area 5 around the lamps 4 in the enclosure 1 is illuminated with approximately the same intensity. The inner walls of the enclosure 1, at least in the area 5 around the lamps, are arranged so that they provide for a good reflection of the light from the lamps 4. A member 7 for circulating the air, for example a fan, is arranged at the outlet 3 in order to lead the air which is to be treated through the apparatus 1.

A number of catalysts 8 are preferably also arranged in the enclosure in the area 5. They can be attached, for example, in a suitable manner to the reflecting inner wall of the enclosure. In the preferred embodiment, the catalysts comprise metal and/or metal oxide, such as noble metals, aluminium oxide, titanium oxide, silicon oxide and mixtures thereof The functioning is as follows. When the apparatus is to be used, the current to the lamps 4 is switched on and the fan 7 begins to rotate. The fan 7 sucks air into the inlet 2, which air flows through the enclosure 1 and through the area 5 where the lamps expose the air to UV radiation. Due to that the walls in the area 5 of the lamps are reflective, the air is exposed to the UV radiation to a higher degree, and thus increasing the efficiency. The spectral distribution of the UV lamps means that ozone molecules ($O_3$) are generated by the oxygen in the air, and especially by radiation at a wavelength of 183.7 nm. At the same time, radiation is generated by the lamps within a wavelength range of 245–400 nm, within which wavelength range the ozone molecules are broken down to oxygen and free radicals, and contaminants to free radicals. Of particular importance are the wavelength of 254 nm and also the wavelength of 364.9 nm, at which increased efficiency in the generation of free radicals is obtained. The catalysts, which are placed in the area 5, render the process more effective by increasing the amount of free radicals per unit of time. By virtue of their susceptibility to oxidation, the free radicals start a chain reaction with the contaminants in the air. The free radicals, and to a certain extent the ozone, effectively break the bonds between the atoms in the molecules which contaminate the air. Microorganisms such as, for example, pathogens are rapidly killed off, and from organic and inorganic matter new free radicals are formed which are more or less reactive. The final products are in the main water vapour, air and carbon dioxide. This embodiment of the apparatus is primarily conceived for purification of air, for example in office premises, schools, gymnasiums, smoking rooms, cabins, toilets.

Figure 2:
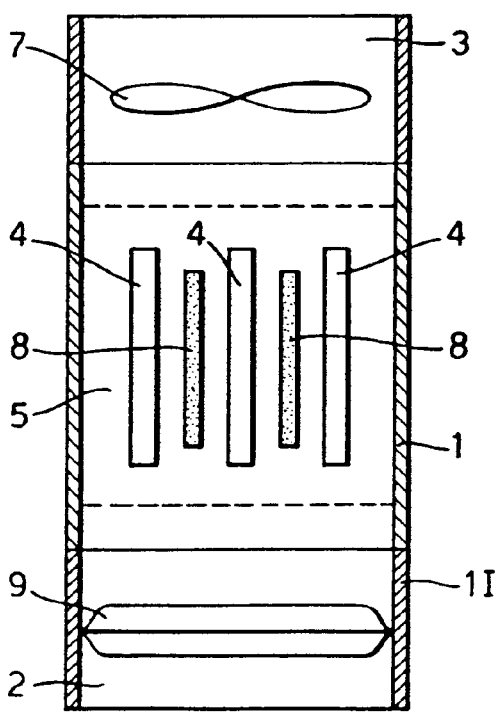
FIG. 2 shows a cross-section of a development of the apparatus according to the invention.

FIG. 2 shows a development of the apparatus according to FIG. 1. In FIG. 2, the same components have the same reference numbers as in FIG. 1. In the apparatus according to FIG. 2, a section 1I of the enclosure 1 has further been connected to the inlet end 2 thereof The new section 1I is arranged with an ozone generator 9 of a suitable type. In the preferred embodiment, the ozone generator 9 is a small dark-discharge unit. In the gap between the electrodes, silicon or similar powder is packed or is mixed with the dielectric material (ceramic), by which means the power is increased and the generator can be made small in size. Other ozone generators can also be conceived, such as electrode plates with a certain air gap where discharges are generated between the plates, and also UV lamps which emit at a certain wavelength. By increasing the amount of ozone, the power is considerably increased. The ozone which is formed by the ozone generator reacts on the one hand directly with the contaminants in the air and is decomposed, and on the other hand is decomposed by the UV lamps to form free radicals in large quantity. This embodiment is primarily conceived for purification of air in large areas and/or areas which are heavily contaminated, such as industrial premises, smoke-damaged premises, stables, etc.

Figure 3:
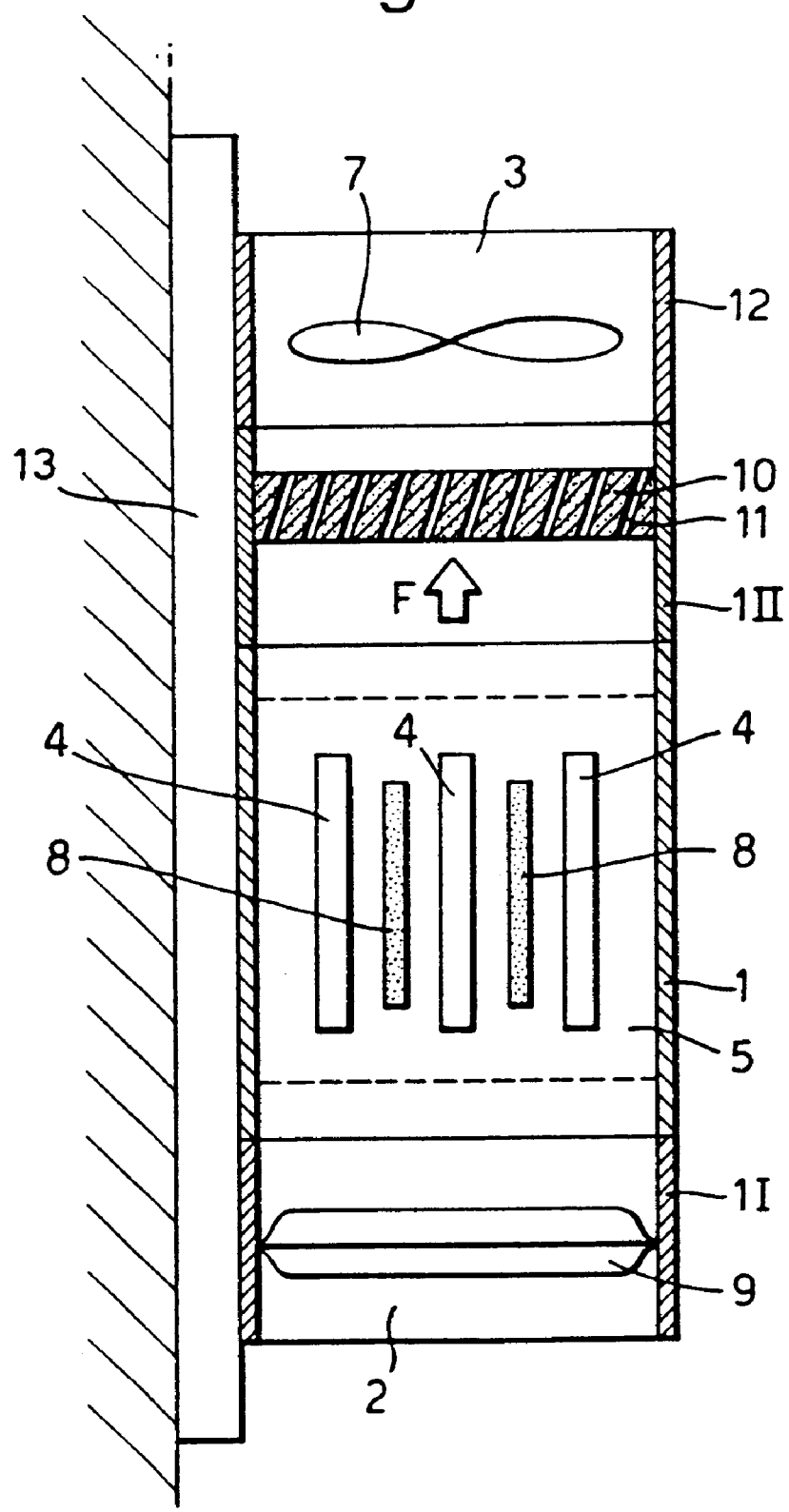
FIG. 3 shows a cross-section of a further development of the apparatus according to the invention.

FIG. 3 shows a third embodiment of the apparatus according to the invention. In this embodiment, a section 1II is placed downstream of the outlet 3 to the apparatus according to FIG. 1 and 2. The section 1II is arranged with a filter 10. The filter 10 consists of porous oxidic ceramics, aluminum oxide, calcium hydroxide, magnesium hydroxide and active charcoal and carbonate. The filter is provided with a number of passages 11, in the preferred embodiment slightly inclined with respect to the direction of flow F in order to increase the contact surface between the filter and the air. The apparatus with the filter is primarily conceived for use in premises with organic gas, where the final products may be unidentifiable, or where there are chlorinated solvents, alcohols, ketones, aromatic compounds, dioxins, hexamine (hexamethylene tetramine), formaldehyde, ammonia, pesticides and herbicides. The abovementioned filter effectively deactivates these final products, and only water vapour, carbon dioxide and air escape from the outlet.

Since both the ozone and in particular the free radicals are short-lived, continuous generation of ozone and free radicals is necessary. The speed of rotation of the fan and consequently the flow rate are adapted to the amount of ozone which is produced in order to obtain an optimal functioning of the apparatus and in order to ensure that no untreated ozone escapes into the environment. The apparatus can be arranged, for example, with a timer which switches the apparatus on at specific time intervals. The flow of air through the apparatus also has the object of cooling the electronic components and warming the filter 10 to increase its efficiency.

By virtue of the modular system with different sections, it is simple to adapt the apparatus to the conditions in which it is to operate. Thus, it is possible to obtain apparatuses with everything from one section 1 with UV lamps to a serial connection of several sections 1 arranged one after the other, ozone generator 9 and filter 10. The fan 7 is also arranged on a section 12, FIG. 3, and it thus forms a modular unit too. The sections can then be mounted on a suitable holder ledge 13, FIG. 3, which is arranged on a suitable support. The holder ledge contains the electrical connection, circuit breaker and optional timer. The electrical connections between the sections and the holder ledge 13 are preferably of the plug-in type. Great flexibility and ease of servicing are obtained in this way since only the faulty section needs to be exchanged or repaired and it is not necessary to dismantle the entire apparatus.

FIG. 4 shows an example of the scope of application and also the advantages of the modular system, for example for sterilizing articles etc., such as operating instruments and catheters which it has not been possible to sterilize, with optimal results, using conventional methods. FIG. 4 shows a cabinet 20 or other well-defined enclosure provided with a door, hatch or similar (not shown) which seals it tight when it is closed. The articles which are to be treated are placed in the cabinet 20, for example on perforated shelves 21. It is also conceivable to use holders specially adapted for the articles which are to be treated. What is important is that the air with free radicals can circulate freely around the articles. Air is drawn in through an inlet 22 provided with a closable valve 23. Connected to the inlet 22 is in the first place a section 1I with an ozone generator which converts oxygen in the incoming air to ozone molecules. Downstream of the section 1I with the ozone generator, as viewed in the direction of flow, there is a second section 1 with UV lamps and catalysts. The radiation from the UV lamps forms ozone and breaks down the latter and the previously formed ozone molecules to give free radicals which flow in large quantity out into the cabinet and sterilize the articles which are placed on the shelves 21. At the upper edge of the cabinet there is a fan section 12, and also a section 1II with filter arranged at an outlet 24, which outlet is provided with a closable valve 25. The fan section 12 generates a flow of air from the inlet 22, through the cabinet and out through the outlet 24. The cabinet is preferably provided with a member which locks the door when the apparatus is in operation, and which indicates this, for example by means of a lamp. The cabinet is also provided with a time control for the apparatus, adapted to the size of the space and to the size and shape of the articles which are to be treated. The cabinet 20 can be of different sizes depending on what is to be treated. It may be adapted, for example, for disinfecting and sterilizing of textiles in the form of operating gowns and the like, which are used in hospitals, the pharmaceutical industry, abattoirs, the electronics industry, etc.

The procedure described above and the apparatus can of course also be used to purify contaminated water, on the one hand, and on the other hand to use water enriched with free radicals for cleaning, disinfecting and sterilizing of instruments, electronic devices, biomaterial and textiles, for example. FIG. 5 shows an example of the use of the present invention for treating water, i.e. decontaminate water or enrich water with free radicals. In this embodiment, one or more sections 1 with UV lamps are placed in the water flow 30. Arranged in a suitable manner upstream of the sections 1 is a connection 31, to which connection 31 a section 1I with ozone generator 9 and a fan section 12 are joined. Between the connection 31 and the water inflow 30 there is some form of nonreturn valve. When circulation of the water through the apparatus is required, i.e. when there is no external flow through the apparatus, a pump 32 is used. The water which flows through is first exposed to ozone from the ozone generator 9, where the ozone is forced down into the water by the fan 7. Ozone is thus added continuously to the water, which ozone water is then immediately irradiated with UV light in order to decompose the ozone and obtain free radicals. When the water is heavily contaminated, or when large amounts of free radicals in the water is needed, an ultrasonic device (33) is placed at the water inflow. High amplitude ultrasonic waves generate free radicals and break contaminants. And in the same way as with the apparatus described above, the apparatus for purifying water can be combined in a number of ways by virtue of the modular system.

The procedure according to the present invention permits a more effective purification, disinfection and sterilization in many areas of application and for many organic and inorganic substances, contaminants and microorganisms in air, in water and on solid objects. Examples of advantages are low energy consumption, no heating of objects, air or water, no chemicals/cleaning agents, small size of the unit, no toxic by-products, long service life, low maintenance and many applications.

It will be understood that the procedure and the apparatuses according to the present invention are not limited to what has been described above, and can instead be modified within the scope of the patent claims which follow.

What is claimed is:

1. An apparatus for treatment of a fluid, comprising:
   an enclosure provided with at least one inlet and at least one outlet,
   at least one ozone generator and at least one UV radiator arranged in the enclosure
   such that the ozone generator generates ozone and, at the same time, the UV radiator breaks down the ozone to free radicals; and
   at least one catalyst arranged close to said ozone generator and said UV radiator to increase the amount of free radicals.

2. The apparatus according to claim 1, wherein the fluid is at least one medium selected from the group consisting of air and water.

3. The apparatus according to claim 1, wherein said UV radiator is at least one UV lamp which emits radiation with a spectral distribution within the range of 180–400 nm.

4. The apparatus according to claim 3, wherein the UV lamp emits radiation at wavelengths of 183.7 nm and 254 nm.

5. The apparatus according to claim 1, wherein the apparatus is provided with a flow member which moves the fluid to be treated through the enclosure.

6. The apparatus according to claim 1, wherein the catalyst is at least one material selected from the group consisting of noble metals, titanium dioxide, aluminum oxide, silicon oxide, and mixtures thereof.

7. The apparatus according to claim 1, further comprising a timer for controlling the time of operation.

8. The apparatus according to claim 1, wherein the apparatus is a modular system with different components distributed in different sections.

9. The apparatus according to claim 1, wherein a liquid flow is led through said enclosure.

10. An apparatus for treatment of a fluid, comprising:
    an enclosure provided with at least one inlet and at least one outlet,
    at least one ozone generator and at least one UV radiator arranged in the enclosure
    such that the ozone generator generates ozone and, at the same time, the UV radiator breaks down the ozone to free radicals; and
    at least one catalyst arranged close to said ozone generator and said UV radiator to increase the amount of free radicals,
    wherein the apparatus is provided with a further ozone generator placed upstream of the said UV radiator.

11. An apparatus for treatment of a fluid, comprising:
    an enclosure provided with at least one inlet and at least one outlet,
    at least one ozone generator and at least one UV radiator arranged in the enclosure
    such that the ozone generator generates ozone and, at the same time, the UV radiator breaks down the ozone to free radicals; and
    at least one catalyst arranged close to said ozone generator and said UV radiator to increase the amount of free radicals,
    wherein a filter is placed downstream of the UV radiator.

12. The apparatus according to claim 11, wherein the filter consists of an oxidic porous ceramic.

13. The apparatus according to claim 12, wherein the filter also includes active charcoal and carbonate.

14. An apparatus for treatment of a fluid, comprising:
    an enclosure provided with at least one inlet and at least one outlet,
    at least one ozone generator and at least one UV radiator arranged in the enclosure
    such that the ozone generator generates ozone and, at the same time, the UV radiator breaks down the ozone to free radicals; and
    at least one catalyst arranged close to said ozone generator and said UV radiator to increase the amount of free radicals,
    wherein a liquid flow is led through said enclosure and
    wherein an ultrasonic device is arranged at the inlet of the liquid flow, so that the liquid flow is subject to ultrasonic action.

15. The apparatus according to claim 14, wherein the liquid flow is connected to a washing apparatus for cleaning, disinfecting or sterilizing solid objects.

* * * * *